(12) United States Patent
Okamura et al.

(10) Patent No.: US 8,579,817 B2
(45) Date of Patent: Nov. 12, 2013

(54) BREAST ULTRASONIC DIAGNOSTIC APPARATUS AND BREAST ULTRASONIC DIAGNOSTIC METHOD

(75) Inventors: Yoko Okamura, Otawara (JP); Naohisa Kamiyama, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 1117 days.

(21) Appl. No.: 12/061,262

(22) Filed: Apr. 2, 2008

(65) Prior Publication Data

US 2008/0249413 A1    Oct. 9, 2008

(30) Foreign Application Priority Data

Apr. 9, 2007  (JP) ................................. 2007-101763

(51) Int. Cl.
    *A61B 8/00*     (2006.01)
(52) U.S. Cl.
    USPC .......................................... 600/443; 600/437
(58) Field of Classification Search
    USPC .......................................... 600/407, 437–447
    See application file for complete search history.

(56) References Cited

U.S. PATENT DOCUMENTS

| | | | |
|---|---|---|---|
| 6,245,017 B1 * | 6/2001 | Hashimoto et al. | 600/447 |
| 6,409,668 B1 | 6/2002 | Wollschlaeger | |
| 7,727,151 B2 * | 6/2010 | Zhang et al. | 600/443 |
| 2006/0291705 A1 * | 12/2006 | Baumann et al. | 382/128 |

FOREIGN PATENT DOCUMENTS

| | | |
|---|---|---|
| JP | 7-67453 | 7/1995 |
| JP | 2002-512835 | 5/2002 |
| JP | 2007-222233 | 9/2007 |

* cited by examiner

*Primary Examiner* — Elmer Chao
(74) *Attorney, Agent, or Firm* — Oblon, Spivak, McClelland, Maier & Neustadt, L.L.P.

(57) ABSTRACT

An ultrasonic diagnostic apparatus, that generates image data of a C-mode image of an examination-target portion based on volume data generated through an ultrasonic scan of an object and for displaying the C-mode image, has a curved C-mode surface generating unit and a curved C-mode image generating unit. The curved C-mode surface generating unit generates, based on the volume data, a curved C-mode surface formed by a curved surface that curves without including a non-visualized portion. The curved C-mode image generating unit generates image data of a curved C-mode image based on data of the curved C-mode surface generated by the curved C-mode surface generating unit.

22 Claims, 10 Drawing Sheets

CURVED C-MODE IMAGE OF CURVED C-MODE SURFACE C1

CURVED C-MODE IMAGE OF CURVED C-MODE SURFACE C2

CURVED C-MODE IMAGE OF CURVED C-MODE SURFACE C3

CURVED C-MODE IMAGE OF CURVED C-MODE SURFACE C4

CURVED C-MODE IMAGE OF CURVED C-MODE SURFACE C1

CURVED C-MODE IMAGE OF CURVED C-MODE SURFACE C2

CURVED C-MODE IMAGE OF CURVED C-MODE SURFACE C3

CURVED C-MODE IMAGE OF CURVED C-MODE SURFACE C4

US 8,579,817 B2

BREAST ULTRASONIC DIAGNOSTIC APPARATUS AND BREAST ULTRASONIC DIAGNOSTIC METHOD

BACKGROUND OF THE INVENTION

1. Field of the Invention

The present invention relates to an ultrasonic diagnostic apparatus and an ultrasonic diagnostic method for generating image data of a C-mode image of an examination-target portion based on volume data generated by performing an ultrasonic scan on an object and displaying the C-mode image.

2. Description of the Related Art

An ultrasonic diagnostic apparatus for realizing an immersion method, which is developed mainly for an ultrasonic examination of breasts held in a group medical examination, are known. In the immersion method, an object such as one of or both of breasts of a patient are immersed in water contained in a special-purpose tank, 2D (sectional) data is generated while moving an ultrasonic probe facing the patient through the tank, and 3D data is also generated based on a plurality of 2D data. Since the use of a mechanical moving stage for vertical movement of the ultrasonic probe permits automatic scans and an existence of water contained in the tank between the probe and the breasts allows images of the entire breasts to be imaged, the immersion method is suitable for a group medical examination system.

To display images of breasts as thoroughly as possible with a minimum number of images particularly in a group medical examination, a C-mode display for displaying C-mode images is performed in ultrasonic diagnosis of breasts.

Breasts are located on a body surface side of a curved thorax. Conventional C-mode display involves disadvantages such as diagnosis of an edge part of a breast in a C-mode image is difficult since an image of the sternum mainly appears and an image of the breast hardly appears on one C-mode image including a part of a breast near a sternum.

SUMMARY OF THE INVENTION

The present invention has taken into consideration the above-described problems, and it is an object of the present invention to provide an ultrasonic diagnostic apparatus and an ultrasonic diagnostic method which can provide images suitable for diagnosis.

To solve the above-described problems, the present invention provides an ultrasonic diagnostic apparatus for generating image data of a C-mode image of an examination-target portion based on volume data generated through an ultrasonic scan of an object and for displaying the C-mode image, the ultrasonic diagnostic apparatus comprising: a curved C-mode surface generating unit configured to generate, based on the volume data, a curved C-mode surface formed by a curved surface that curves without including a non-visualized portion; and a curved C-mode image generating unit configured to generate image data of a curved C-mode image based on data of the curved C-mode surface generated by the curved C-mode surface generating unit.

To solve the above-described problems, the present invention provides an ultrasonic diagnostic method for generating image data of a C-mode image of an examination-target portion based on volume data generated through an ultrasonic scan of an object and for displaying the C-mode image, the method comprising: a curved C-mode surface generating step of generating, based on the volume data, a curved C-mode surface formed by a curved surface that curves without including a non-visualized portion; and a curved C-mode image generating step of generating image data of a curved C-mode image based on data of the curved C-mode surface generated by the curved C-mode surface generating step.

DESCRIPTION OF THE PREFERRED EMBODIMENTS

An ultrasonic diagnostic apparatus and an ultrasonic diagnostic method according to embodiments of the present invention will be described with reference to the accompanying drawings. A technical method employed by an ultrasonic diagnostic apparatus according to the embodiment is effective when an object such as breasts and organs (e.g., a liver, a pancreas, and so on) is set as examination target. To make the description more specific, it is assumed that breasts are set as the examination targets of an ultrasonic diagnostic apparatus according to the embodiment.

Figure 1:
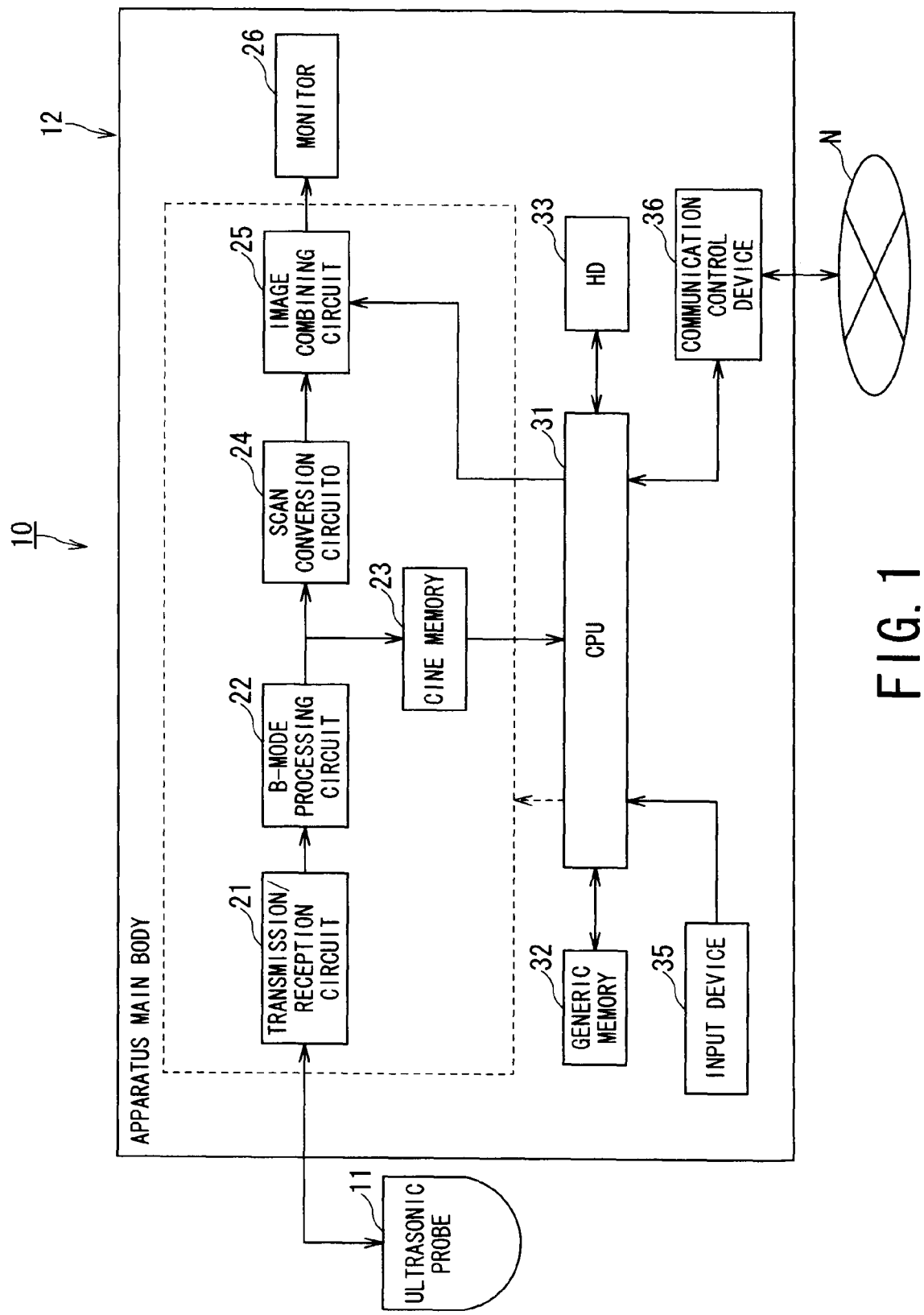
FIG. 1 is a diagram showing a configuration of an ultrasonic diagnostic apparatus according to an embodiment of the present invention.

FIG. 1 is a diagram showing a configuration of an ultrasonic diagnostic apparatus according to an embodiment of the present invention.

FIG. 1 shows an ultrasonic diagnostic apparatus 10 according to the embodiment. The ultrasonic diagnostic apparatus 10 realizes an immersion method, which is developed mainly for an ultrasonic examination of breasts held in a group medical examination. In the immersion method, one of or both of breasts of a patient are immersed in water contained in a special-purpose tank (not shown), 2D (sectional) data is generated while moving an ultrasonic probe facing the patient through the tank, and 3D data is also generated based on a plurality of pieces of 2D data. Since the use of a mechanical moving stage for vertical movement of the ultrasonic probe permits automatic scans and existence of water contained in the tank between the probe and the breasts allows images of the entire breasts to be imaged, the immersion method is suitable for a group medical examination system. In addition, the ultrasonic diagnostic apparatus 10 can be employed in an examination of predetermined organs, such as a liver and a pancreas, in addition to an examination of breasts.

The ultrasonic diagnostic apparatus 10 generally has an ultrasonic probe 11 and an apparatus main body 12.

The ultrasonic probe 11 transmits and receives ultrasonic waves with a plurality of ultrasonic transducers arranged at a distal end portion thereof. The ultrasonic transducers may be electroacoustic ultrasonic transducers. The ultrasonic transducers convert electric pulses into ultrasonic pulses at the time of transmission of ultrasonic waves and also convert ultrasonic signals into electric signals at the time of reception of ultrasonic waves. The ultrasonic probe 11 is classified into a 1D (a single row only for an azimuth-direction operation) array probe, a 1.5D array (electronically focused but not operated in an elevation-direction) probe, and a 2D array (a fine pitch array for a wide-range three-dimensional operation) probe depending on types of array converters. To actively acquire volume data of living bodies, it is desirable to employ a 2D array probe among these kinds.

In addition, the ultrasonic probe 11 may be a 1D array probe or a 2D array probe, or may be a mechanical 3D probe that has a swinging function, acquires a plurality of sectional images while sequentially changing scanning sections, and ultimately acquires the volume data.

The apparatus main body 12 includes a transmission/reception circuit 21, a B-mode processing circuit 22, a cine memory 23, a scan conversion circuit 24, an image combining circuit 25, and a monitor 26.

The transmission/reception circuit 21 includes a transmission unit and a reception unit, not shown. The transmission unit includes a rate pulse generating circuit, a transmission delay circuit, and a pulser circuit. The rate pulse generating circuit generates rate pulses that decide an interpulse period of irradiated ultrasonic pulses. The transmission delay circuit decides a convergence time and a deflection angle of an ultrasonic beam at the time of the transmission of the ultrasonic waves and also decides timings of driving N ultrasonic transducers, where N is a positive integer. The pulser circuit generates high-voltage pulses for driving the ultrasonic transducers.

The rate pulse generating circuit included in the transmission unit of the transmission/reception circuit 21 supplies the transmission delay circuit with rate pulses for deciding the interpulse period of irradiated ultrasonic pulses. The transmission delay circuit includes independent delay circuits, the number of which is twice (2N) as many as that of the ultrasonic transducers for use in transmission of ultrasonic waves. To obtain a narrow beam width at the time of transmission of ultrasonic waves, the transmission delay circuit applies a delay time for converging the ultrasonic waves at a predetermined depth and a display time for transmitting the ultrasonic waves in a predetermined direction to the rate pulse. The transmission delay circuit then supplies the rate pulse to the pulser circuit.

The pulser circuit has 2N independent driving circuits, the number of which is the same as that of the delay circuits. The pulser circuit drives the ultrasonic transducers included in the ultrasonic probe 11 and forms driving pulses for irradiating ultrasonic waves to a patient.

Some of ultrasonic waves irradiated to a breast of the patient are reflected by a boundary or a tissue between organs having different acoustic impedances. The reflected wave newly generates an ultrasonic pulse having a center frequency $2f_0$ due to nonlinear characteristics of the tissue. Accordingly, ultrasonic pulses (fundamental components) having a center frequency $f_0$ set at the time of transmission of ultrasonic waves and ultrasonic pulses (harmonic components) having a center frequency $2f_0$ coexist in ultrasonic waves reflected by the tissue and returning to the ultrasonic probe 11. The reception unit included in the transmission/reception circuit 21 includes a BPF (Band Pass Filter), a preamplifier circuit, an A/D (Analog/Digital) converting circuit, and a phasing/adding circuit. The BPF extracts the fundamental components or the harmonic components of the reception signal. The preamplifier circuit amplifies a feeble electric signal converted by the ultrasonic transducers. The A/D converting circuit digitalizes the reception signal supplied from the preamplifier circuit. The phasing/adding circuit has a beamformer circuit and an adding circuit.

To obtain a narrow reception beam width, the beamformer circuit sequentially changes a convergence delay time for converging ultrasonic waves from a predetermined depth and a reception directivity of the ultrasonic beam to apply a delay time for scanning in the patient to the digitalized reception signal. The adding circuit adds the signals output from the beamformer circuit.

The B-mode processing circuit 22 generates RAW data (data before undergoing scan conversion processing) for B-mode images (tomograms) based on the digital input signal supplied from the transmission/reception circuit 21. More specifically, the B-mode processing circuit 22 includes a logarithmic transformation circuit and an envelope detection circuit, not shown. The logarithmic transformation circuit performs logarithmic transformation of the amplitude of the digital input signal supplied from the transmission/reception circuit 21 to relatively strengthen a weak signal. The envelope detection circuit performs an envelope detection operation on the digital signal logarithmically transformed by the logarithmic transformation circuit to detect an envelope of the amplitude.

Meanwhile, a color-Doppler-mode processing circuit (not shown) may be provided in parallel to the B-mode processing circuit 22. The color-Doppler-mode processing circuit performs signal processing for generating velocity distribution data using a cosine component velocity code (e.g., 8 bits and 256-step gradation) of ultrasonic-scan-line-direction components (hereinafter, referred to as "cosine components") relative to an absolute velocity of a moving object, e.g., blood flow, to generate RAW data for color Doppler images (color blood flow images, CFM (Color Flow Mapping)). The color-Doppler-mode processing circuit has a quadrature detection circuit, an FFT analysis circuit, and a calculating circuit. The quadrature detection circuit converts the digital input signal supplied from the transmission/reception circuit 21 into a complex (Doppler) signal having a real part and an imaginary part. The FFT analysis circuit performs FFT (Fast Fourier Transform) analysis on the complex components orthogonal to each other. The calculating circuit calculates the center of the spectrum (an average velocity of the cosine components relative to the blood flow direction) resulting from the FFT analysis and a variance (turbulence of the blood flow).

The cine memory 23 is a storage device constituted by a nonvolatile semiconductor memory or the like. The cine memory 23 stores, for example, RAW data of live images corresponding to a plurality of frames just before the ultrasonic diagnostic apparatus 10 finishes (freezes) the collection of images. The cine memory 23 has a capacity for storing a plurality of pieces of RAW data and consecutively stores RAW data until it receives a freeze command sent from a CPU 31. Generally, a loop method is employed in storage of the cine memory 23. More specifically, when the size of the stored RAW data exceeds the capacity of the cine memory 23, new RAW data is written (overwritten) after RAW data having the oldest storage time is deleted, whereby the cine memory 23 stores the latest RAW data.

The scan conversion circuit 24 converts the RAW data of live images output from the B-mode processing circuit 22 into standard TV signals (TV format signals) to generate image data of the live images.

The image combining circuit 25 generates display data of the live images based on the image data of the live images output from the scan conversion circuit 24 and converts the display data into analog data. In addition, the image combining circuit 25 generates display data based on image data (which will be described later) of curved C-mode images output from a control device (CPU: central processing unit) 31, which will be described later, and converts the display data into analog data. The image combining circuit 25 also combines images and textual information of various parameters and scales and outputs image data of the combined images to the monitor 26 as video signals.

The monitor 26 displays live images and curved C-mode images based on the image data output from the image combining circuit 25.

Additionally, the ultrasonic diagnostic apparatus 10 includes the CPU 31, a generic memory 32, a hard disk (HD) 33, an input device 35, and a communication control device 36.

According to programs stored in the generic memory 32 and the HD 33 and instruction entered through the input device 35, the CPU 31 controls operations of the transmission/reception circuit 21, the signal processing circuit 22, the cine memory 23, the scan conversion circuit 24, and the image combining circuit 25.

The generic memory 32 is a storage device constituted by a nonvolatile semiconductor memory or the like. The generic memory 32 stores an IPL (Initial Program Loading), a BIOS (Basic Input/Output System), and various application programs related to ultrasonic diagnosis. The various application programs related to ultrasonic diagnosis include a program for displaying of live images and program for playback of images. The generic memory 32 also functions as a working memory of the CPU 31.

The HD 33 is a storage device constituted by a metal disk having a magnetic body applied or deposited thereon. Data can be written on or read out from the HD 33 with an HDD (Hard Disk Drive), not shown. The HD 33 stores the volume data and image data of curved C-mode images. The HD 33 may also store various application programs related to ultrasonic diagnosis instead of the generic memory 32.

The input device 35 includes, for example, a mouse, a trackball, a mode switch, and a keyboard. The input device 35 is for imaging, into the apparatus main body 12, various instructions entered by operators, an instruction for setting a region of interest (ROI), an instruction for freeze, and various image quality condition setting instructions.

The communication control device 36 controls the communication according to a corresponding specification. The communication control device 36 has a function to allow the ultrasonic diagnostic apparatus 10 to be connected to a network N, such as a hospital backbone LAN (Local Area Network), through a telephone line. Accordingly, the ultrasonic diagnostic apparatus 10 can be connected to the network N that resides outside of the ultrasonic diagnostic apparatus 10 through the communication control device 36.

Figure 2:
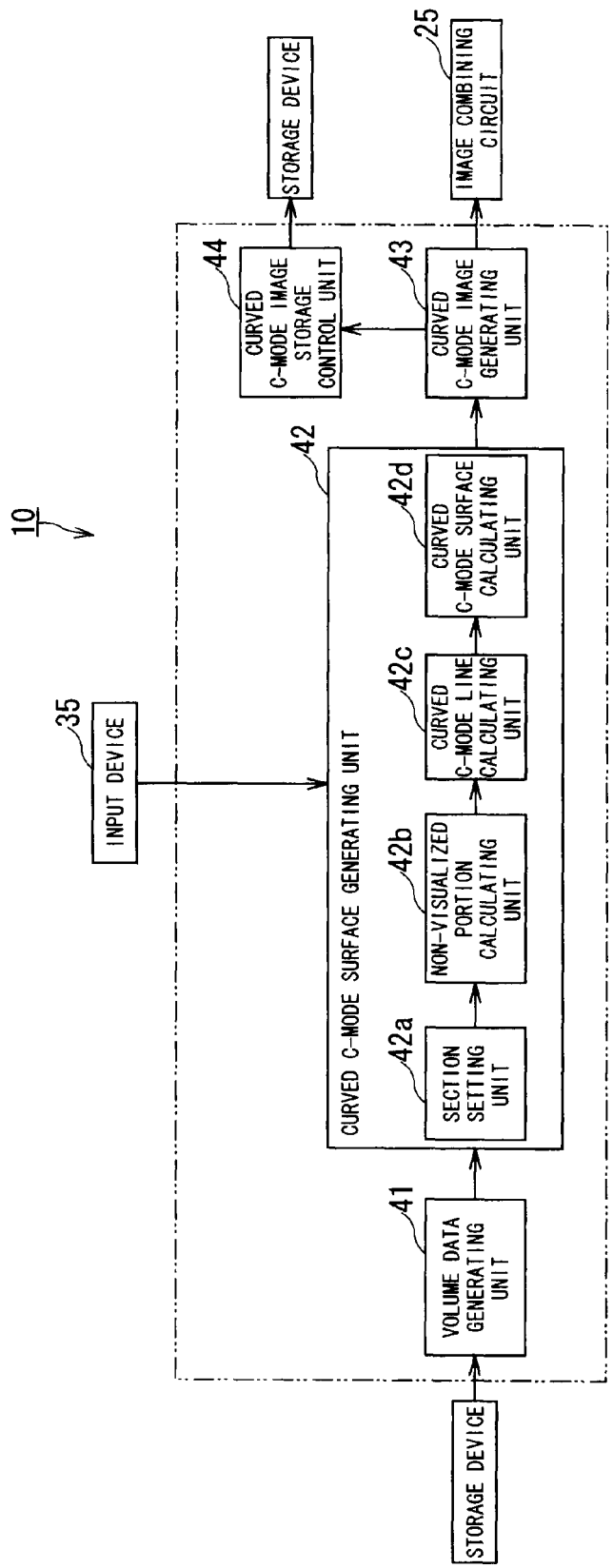
FIG. 2 is a diagram showing a function of the ultrasonic diagnostic apparatus according to the embodiment of the present invention.

FIG. 2 is a diagram showing a function of the ultrasonic diagnostic apparatus 10 according to the embodiment of the present invention.

The CPU 31 (shown in FIG. 1) executes programs, whereby the ultrasonic diagnostic apparatus 10 functions as a volume data generating unit 41, a curved C-mode surface generating unit 42, a curved C-mode image generating unit 43, and a curved C-mode image storage control unit 44. Although each of the units 41 to 44 constituting the ultrasonic diagnostic apparatus 10 is described as a unit functions through software, these units may be provided in the ultrasonic diagnostic apparatus 10 as hardware.

The volume data generating unit 41 has a function to three-dimensionally rearrange ultrasonic scan line signal sequences based on the RAW data stored in the cine memory 23 to generate (reconstruct) volume data.

The curved C-mode surface generating unit 42 has a function to generate a curved C-mode surface formed by a curved surface that curves without including a non-visualized portion based on the volume data generated by the volume data generating unit 41.

FIGS. 3 to 6 are conceptual diagrams for describing arrangements of curved C-mode surfaces.

Figure 3:
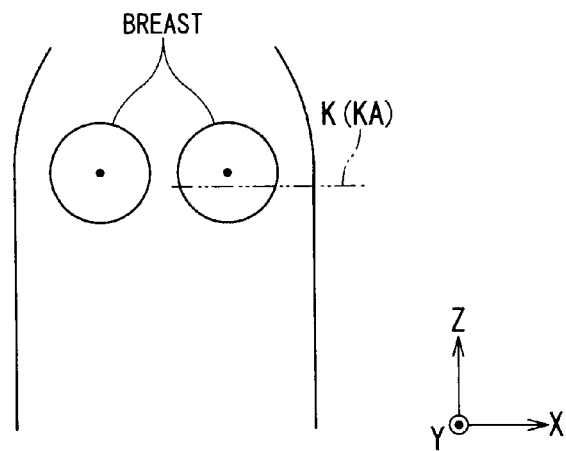
FIG. 3 is a diagram of an X-Z cross-section showing a position of an axial section so as to explain, using the axial section, an arrangement of a curved C-mode surface.
Figure 4:
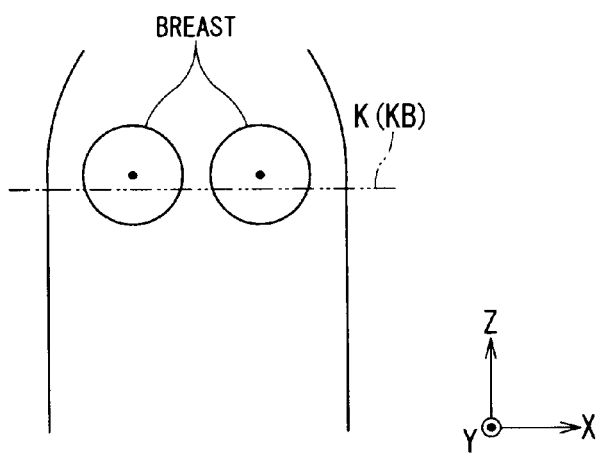
FIG. 4 is a diagram of an X-Z cross-section showing a position of an axial section so as to explain, using the axial section, an arrangement of a curved C-mode surface.

FIGS. 3 and 4 are respectively a diagram of an X-Z cross-section showing a position of an axial section so as to explain, using the axial section, an arrangement of the curved C-mode surface, when a surface (X-Y section) vertical to a body axis is the axial section. For example, FIGS. 3 and 4 are respectively the diagram of the X-Z cross-section showing the position of an axial section K including one of (both of) the breasts of the patient so as to explain, using the axial section K, an arrangement of the curved C-mode surface. FIG. 3 is the diagram of the X-Z cross-section showing an axial section KA including only one of the breasts of the patient, whereas FIG. 4 is the diagram of the X-Z cross-section showing an axial section KB including both of the breasts of the patient.

Figure 5:
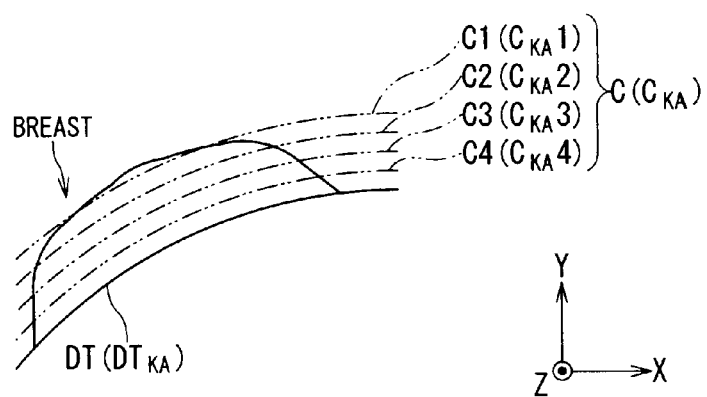
FIG. 5 is a diagram of an X-Y section showing an example of the curved C-mode surfaces as curved C-mode lines on the axial section KA shown in FIG. 3.

FIG. 5 is a diagram of an X-Y section showing an example of the curved C-mode surfaces as the curved C-mode lines on the axial section KA shown in FIG. 3.

As shown in FIG. 5, the curved C-mode surface generating unit 42 generates curved C-mode surfaces C (FIG. 5 shows, for example, four curved C-mode surfaces C1, C2, C3, and C4) formed by curved surfaces that curve toward a body surface side of a thorax surface DT without including a non-visualized portion of the patient, e.g., the thorax surface DT, on the axial section KA included in the volume data generated by the volume data generating unit 41. Note that FIG. 5 shows the thorax surface DT and the curved C-mode surfaces C (the curved C-mode surfaces C1, C2, C3, and C4) as a thorax line $DT_{KA}$ on the axial section KA and curved C-mode lines $C_{KA}$ (curved C-mode lines $C_{KA}1$, $C_{KA}2$, $C_{KA}3$, and $C_{KA}4$) on the axial section KA, respectively.

Figure 6:
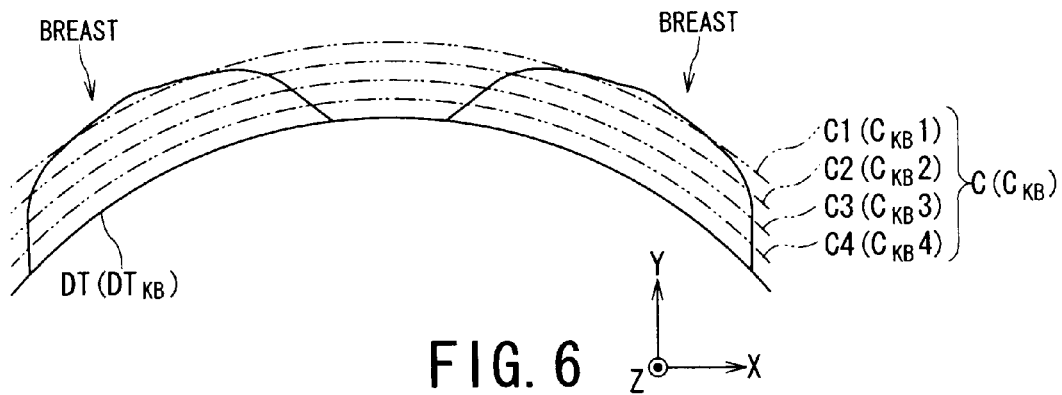
FIG. 6 is a diagram of an X-Y section showing an example of the curved C-mode surfaces as curved C-mode lines on the axial section KB shown in FIG. 4.

FIG. 6 is a diagram of an X-Y section showing an example of the curved C-mode surfaces as the curved C-mode lines on the axial section KB shown in FIG. 4.

As shown in FIG. 6, the curved C-mode surface generating unit 42 generates curved C-mode surfaces C (FIG. 6 shows, for example, four curved C-mode surfaces C1, C2, C3, and C4) formed by curved surfaces that curve toward the body surface side of the thorax surface DT without including the thorax surface DT on the axial section KB included in the volume data generated by the volume data generating unit 41. FIG. 6 shows the thorax surface DT and the curved C-mode surfaces C (the curved C-mode surfaces C1, C2, C3, and C4) as a thorax line $DT_{KB}$ on the axial section KB and curved C-mode lines $C_{KB}$ (curved C-mode lines $C_{KB}1$, $C_{KB}2$, $C_{KB}3$, and $C_{KB}4$) on the axial section KB, respectively.

More specifically, the curved C-mode surface generating unit 42 includes a section setting unit 42*a*, a non-visualized portion calculating unit 42*b*, a curved C-mode line calculating unit 42*c*, and a curved C-mode surface calculating unit 42*d*.

The section setting unit 42*a* has a function to set a specific axial section, e.g., an axial section including a mamilla of the patient (hereinafter, referred to as "mamillary section") based on the volume data generated by the volume data generating unit 41. The section setting unit 42*a* automatically sets the specific axial section using image recognition. Alternatively, an operator selects image data of a desired axial section using the input device 35 while watching images of a plurality of axial sections generated and displayed based on the volume data, whereby the section setting unit 42*a* manually sets the specific axial section. When the mamillary section is set as the specific axial section, the section setting unit 42*a* may set a mamillary section that includes only one of the breasts of patient or a mamillary section that includes both of the breasts of the patient. A description will be given below for a case where the section setting unit 42*a* sets a mamillary section that includes only one of the breasts of the patient.

The non-visualized portion calculating unit 42*b* has a function to calculate a non-visualized portion on the specific axial section, e.g., a thorax line formed on the body surface, based on the image data of the specific axial section set by the section setting unit 42*a*. If a C-mode image includes a thorax surface, since an image of a sternum appears, the entire image data of the C-mode image can not be used in diagnosis of breasts.

Figure 7:
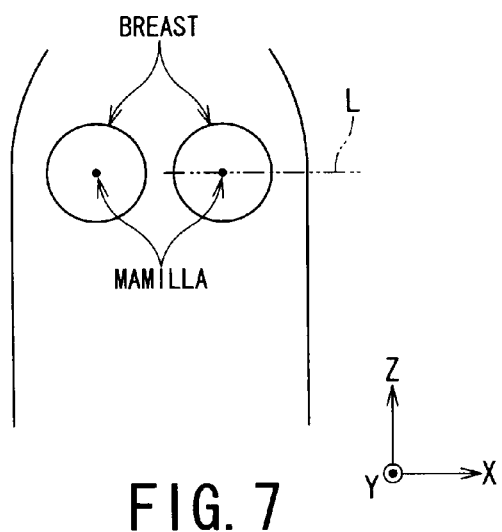
FIG. 7 is a diagram of an X-Z cross-section showing a position of a mamillary section as a specific axial section.
Figure 8:
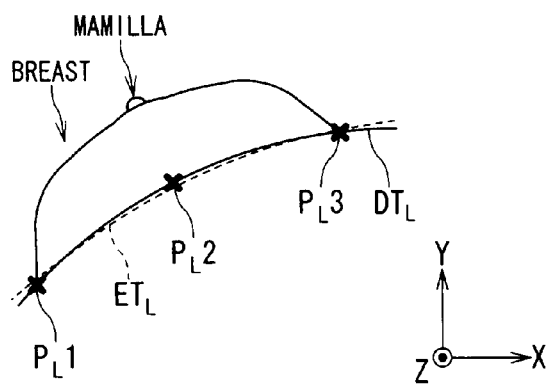
FIG. 8 is a conceptual diagram so as to explain a first method for calculating a thorax line on the mamillary section shown in FIG. 7.

FIG. 7 is a diagram of an X-Z cross-section showing a position of the mamillary section set by the section setting unit 42*a* as the specific axial section. FIG. 8 is a conceptual diagram so as to explain a first method for calculating a thorax line on the mamillary section shown in FIG. 7.

FIG. 8 is a diagram of the X-Y section showing an imaged thorax line $DT_L$ on the mamillary section L shown in FIG. 7 and a calculated thorax line $ET_L$ on the mamillary section L. As shown in FIG. 8, an operator plots three or more thorax points $P_L$, e.g., three thorax points $P_L 1$, $P_L 2$, and $P_L 3$, at positions corresponding the imaged thorax line $DT_L$ on the mamillary section L using the input device 35 while watching an image of the mamillary section L generated and displayed based on the volume data. The non-visualized portion calculating unit 42*b* then calculates a curve (e.g., arc) decided by the thorax points $P_L 1$, $P_L 2$, and $P_L 3$ as the calculated thorax line $ET_L$ on the mamillary section L.

Figure 9:
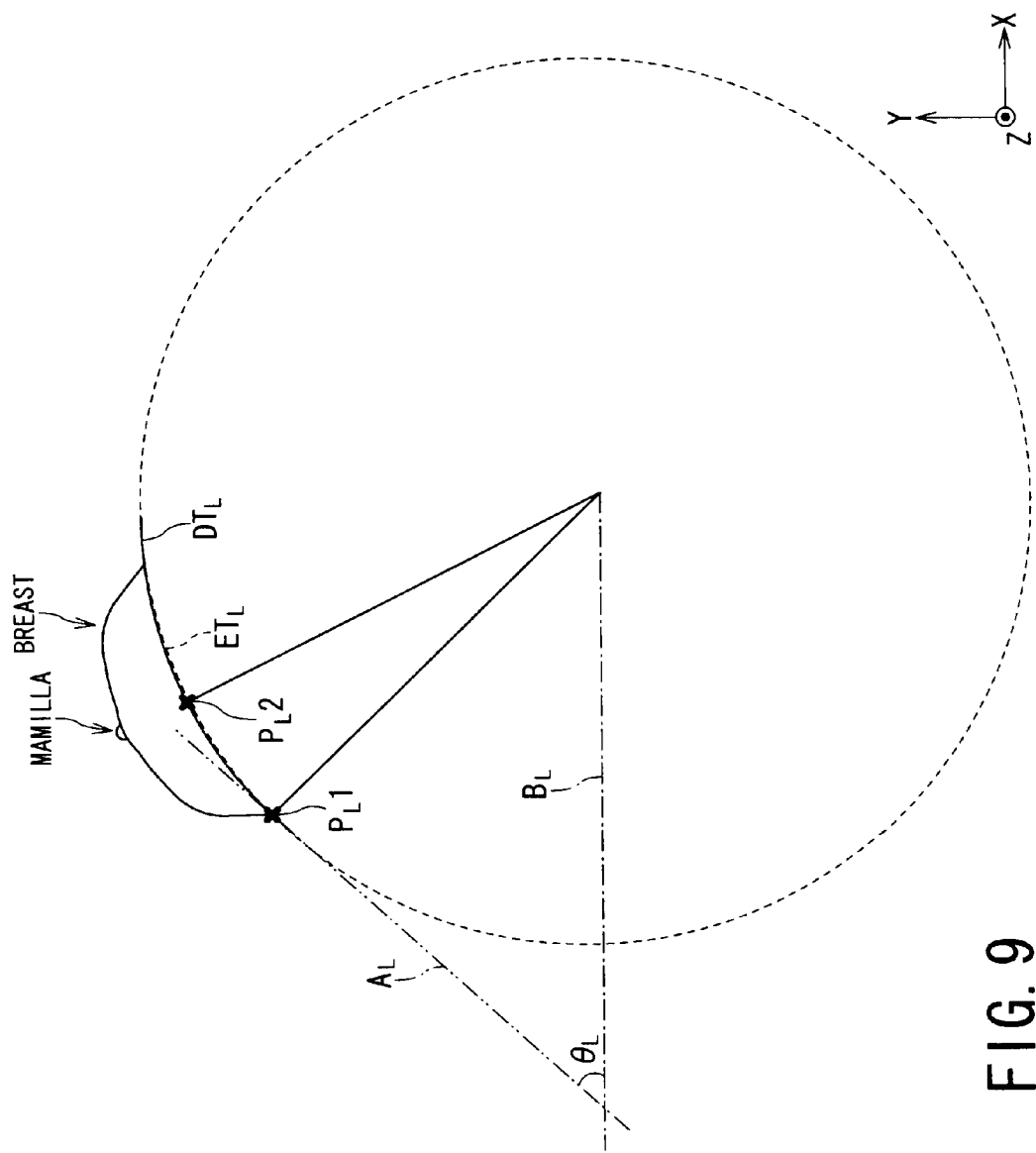
FIG. 9 is a conceptual diagram so as to explain a second method for calculating a thorax line on the mamillary section shown in FIG. 7.

FIG. 9 is a conceptual diagram so as to explain a second method for calculating a thorax line on the mamillary section shown in FIG. 7.

FIG. 9 is a diagram of the X-Y section showing an imaged thorax line $DT_L$ on the mamillary section L shown in FIG. 7 and a calculated thorax line $ET_L$ on the mamillary section L. As shown in FIG. 9, an operator plots two or more thorax points $P_L$, e.g., two thorax points $P_L 1$ and $P_L 2$, at positions corresponding to the imaged thorax line $DT_L$ on the mamillary section L using the input device 35 while watching an image of the mamillary section L generated and displayed based on the volume data. The non-visualized portion calculating unit 42*b* then calculates, as the calculated thorax line $ET_L$ on the mamillary section L, an arc of a circle that passes through the thorax points $P_L 1$ and $P_L 2$ when an angle $\theta_L$ between a tangent $A_L$ passing through the thorax point $P_L 1$ and a horizontal line $B_L$ is equal to a predetermined angle, e.g., 70 degrees.

Furthermore, as a third method for calculating a thorax line on the mamillary section L shown in FIG. 7, the non-visualized portion calculating unit 42*b* can semi-automatically determine the calculated thorax line on the mamillary section based on image data of the mamillary section generated and displayed based on the volume data. When the calculated thorax line on the mamillary section is semi-automatically determined, an operator plots a plurality of thorax points at positions corresponding to the imaged thorax line on the mamillary section using the input device 35 while watching an image of the mamillary section generated and displayed based on the volume data. The non-visualized portion calculating unit 42*b* then calculates, as the calculated thorax line on the mamillary section, a line smoothly connecting the plurality of thorax points and image-imaged high-luminance points on the mamillary section.

In addition, as a fourth method for calculating a thorax line on the mamillary section L shown in FIG. 7, the non-visualized portion calculating unit 42*b* can automatically determine the calculated thorax line on the mamillary section based on the image data of the mamillary section generated and displayed based on the volume data. When the calculated thorax line on the mamillary section is automatically determined, the non-visualized portion calculating unit 42*b* calculates, as the calculated thorax line on the mamillary section, a line smoothly connecting image-imaged high-luminance points on the mamillary section.

In addition, the curved C-mode line calculating unit 42*c* shown in FIG. 2 has a function to calculate a curved C-mode line on a specific axial section based on the calculated thorax line on the specific axial section determined by the non-visualized portion calculating unit 42*b*.

Figure 10A:
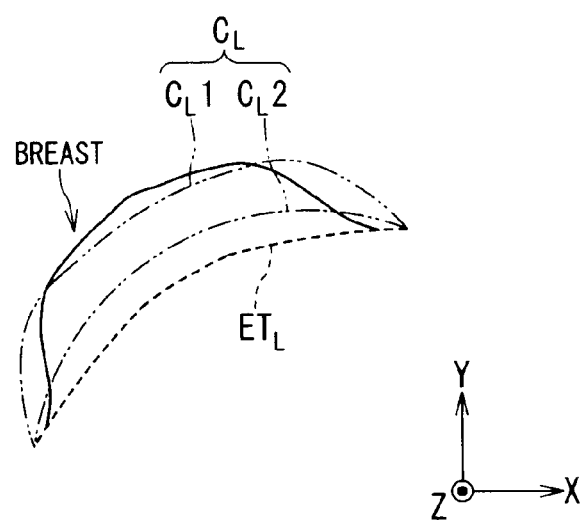
FIGS. 10A to 10B are respectively a conceptual diagram showing an example of method for calculating a curved C-mode line on the mamillary section shown in FIG. 7.
Figure 10B:
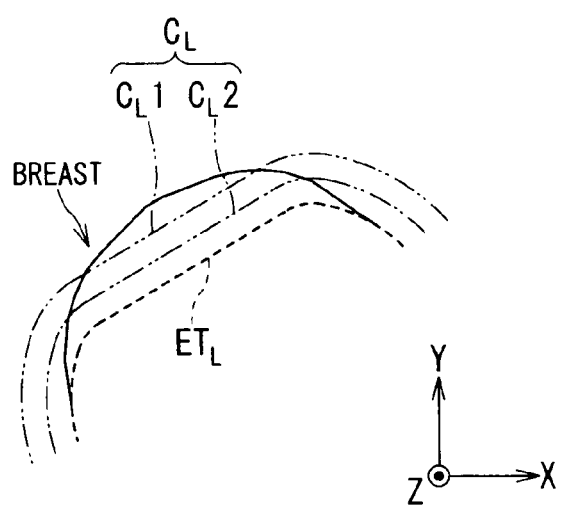

FIGS. 10A and 10B are respectively a conceptual diagram showing an example of method for calculating curved C-mode line on the mamillary section shown in FIG. 7.

FIG. 10A is a diagram of the X-Y section showing curved C-mode lines $C_L$ (FIG. 10A shows, for example, two curved C-mode lines $C_L 1$ and $C_L 2$) that share ends of the calculated thorax line $ET_L$ on the mamillary section L shown in FIG. 7 and that curve toward the body surface side of the patient (upward in FIG. 10A). The curved C-mode lines $C_L$ on the mamillary section L are calculated by changing a diameter and a curvature of a circle that passes through the both ends of the calculated thorax line $ET_L$ on the mamillary section L based on an arc (that curves toward the body surface side from the both ends of the thorax lines $ET_L$) of the circle. An operator may change the diameter and curvature of the circle using the input device 35. In such a case, it is preferable to display a colored arc of the circle passing through the both ends of the thorax line $ET_L$.

On the other hand, FIG. 10B shows curved C-mode lines $C_L$ (FIG. 10B shows, for example, two curved C-mode lines $C_L 1$ and $C_L 2$) that are obtained by translating the thorax line $ET_L$, set by the non-visualized portion calculating unit 42*b* based on the mamillary section L shown in FIG. 7, toward the body surface side of the thorax line $ET_L$ without changing the shape of the thorax line $ET_L$. Meanwhile, an operator may change a thickness between the curved C-mode lines $C_L$ using the input device 35.

Here, there is a case where the number of curved C-mode lines $C_L$ (curved C-mode surfaces C generated based on the curved C-mode lines $C_L$) is preset. In such a case, the curved C-mode line calculating unit 42c calculates the preset number of the curved C-mode lines $C_L$ on the mamillary section L according to the methods for calculating the curved C-mode lines $C_L$ described using FIGS. 10A and 10B.

Figure 11A:
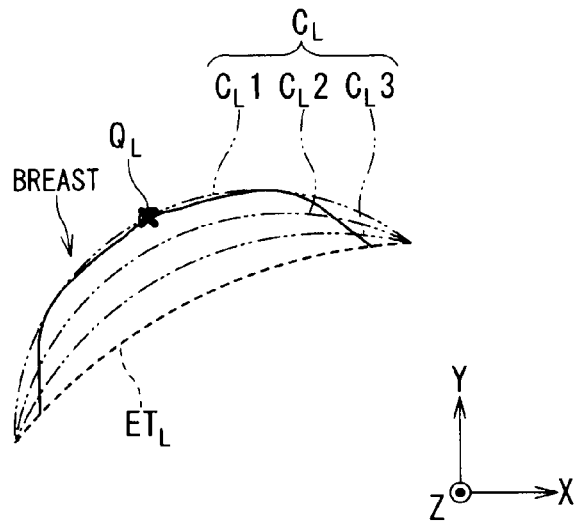
FIGS. 11A to 11B are respectively a conceptual diagram showing an example of method for calculating a curved C-mode line employed when the number of the curved C-mode lines is preset.
Figure 11B:
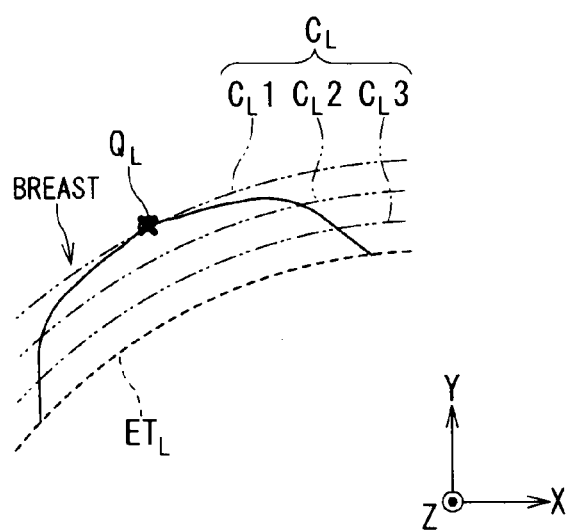

FIGS. 11A and 11B are respectively a conceptual diagram showing an example of method for calculating curved C-mode line employed when the number of the curved C-mode lines is preset.

When the number of the curved C-mode lines $C_L$ is preset, an operator plots a point at a position corresponding to a specific image-imaged portion, e.g., a mamilla point $Q_L$ at a position corresponding to a mamilla, on the mamillary section L using the input device 35 while watching an image of the mamillary section L generated and displayed based on the volume data as shown in FIG. 11A. The curved C-mode line calculating unit 42c calculates a curved C-mode line $C_L1$ that shares ends of the calculated thorax line $ET_L$ on the mamillary section L and curves from the apex mamilla point $Q_L$. In addition, the curved C-mode line calculating unit 42c inserts curved C-mode lines $C_L$ (curved C-mode lines $C_L2$, $C_L3$, ...) that share the ends of the thorax line $ET_L$ between the thorax line $ET_L$ and the curved C-mode line $C_L1$ according to the preset number of the curved C-mode lines $C_L$.

Alternatively, when the number of curved C-mode lines $C_L$ is preset, an operator plots the mamilla point $Q_L$ at a position corresponding to an image-imaged mamilla on the mamillary section L using the input device 35 while watching an image of the mamillary section L generated and displayed based on the volume data as shown in FIG. 11B. The curved C-mode line calculating unit 42c then translates the thorax line $ET_L$ calculated by the non-visualized portion calculating unit 42b toward the body surface side without changing the shape of the thorax line $ET_L$ and calculates a curved C-mode line $C_L1$ passing through the mamilla point $Q_L$ on the mamillary section L. In addition, the curved C-mode line calculating unit 42c inserts curved C-mode lines $C_L$ (curved C-mode lines $C_L2$, $C_L3$, ...), obtained by translating the thorax line $ET_L$ set by the non-visualized portion calculating unit 42b toward the body surface side without changing the shape of the thorax line, between the thorax line $ET_L$ and the curved C-mode line $C_L1$ according to the preset number of curved C-mode lines $C_L$.

In addition to the case where the number of curved C-mode lines $C_L$ is preset, there is a case where a length between the curved C-mode lines $C_L$ (curved C-mode surfaces C generated based on the curved C-mode lines $C_L$) is preset. In such a case, the curved C-mode line calculating unit 42c calculates the curved C-mode line $C_L$ according to the preset length.

Additionally, the curved C-mode surface calculating unit 42d shown in FIG. 2 has a function to calculate a curved C-mode surface based on a curved C-mode line on a specific axial section determined by the curved C-mode line calculating unit 42c. For example, the curved C-mode surface calculating unit 42d calculates a curved C-mode surface by horizontally moving the curved C-mode line on the specific axial section in the axial direction (in the Z-axis direction).

The curved C-mode image generating unit 43 has a function to convert RAW data of the curved C-mode surfaces generated by the curved C-mode surface generating unit 42 into standard TV signals to generate image data of curved C-mode images. The curved C-mode images are displayed on the monitor 26 through the image combining circuit 25.

FIGS. 12A to 12D are respectively a conceptual diagram showing an example of displayed curved C-mode image.

Figure 12A:
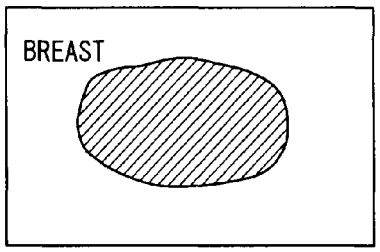
FIGS. 12A to 12D are respectively a conceptual diagram showing an example of displayed curved C-mode image.
Figure 12A:
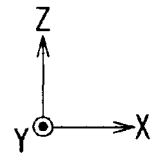
Figure 12B:
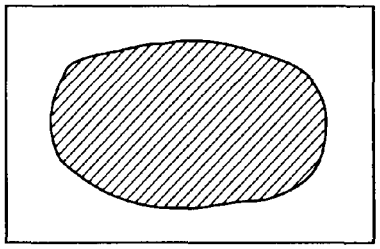
Figure 12B:
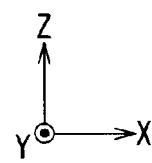
Figure 12C:
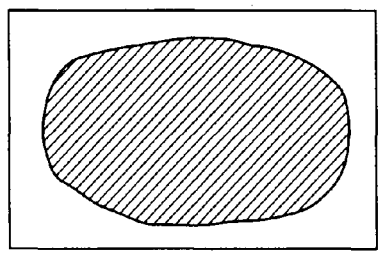
Figure 12C:
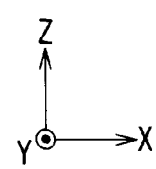
Figure 12D:
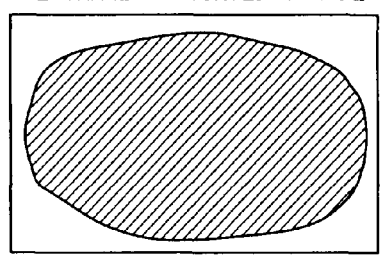
Figure 12D:
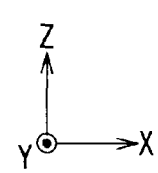

FIG. 12A shows a curved C-mode image of the curved C-mode surface C1 (shown in FIG. 5) generated by the curved C-mode surface generating unit 42. FIG. 12B shows a curved C-mode image of the curved C-mode surface C2 (shown in FIG. 5) generated by the curved C-mode surface generating unit 42. FIG. 12C shows a curved C-mode image of the curved C-mode surface C3 (shown in FIG. 5) generated by the curved C-mode surface generating unit 42. In addition, FIG. 12D shows a curved C-mode image of the curved C-mode surface C4 (shown in FIG. 5) generated by the curved C-mode surface generating unit 42. FIGS. 12A to 12D show curved C-mode surfaces C including only one of the breasts of the patient.

As shown in FIGS. 12A to 12D, since the image data of curved C-mode images does not include a thorax surface that is a non-visualized portion, and the image of the sternum dose not appear, the entire image data of the curved C-mode images can be used for diagnosis of breasts.

Meanwhile, when the section setting unit 42a of the curved C-mode surface generating unit 42 sets a mamillary section that includes both of the breasts of the patient, the curved C-mode surface generating unit 42 can generate curved C-mode surfaces including both of the breasts. Accordingly, curved C-mode images including both of the breasts are displayed on the monitor 26. Additionally, even when the section setting unit 42a of the curved C-mode surface generating unit 42 sets a mamillary section including only one of the breasts of the patient, the curved C-mode surface generating unit 42 can generate curved C-mode surfaces including both of the breasts based on the curved C-mode surface calculated based on the mamillary section including only one of the breasts. Accordingly, curved C-mode images including both of the breasts are displayed on the monitor 26.

FIGS. 13A to 13D are respectively a conceptual diagram showing an example of displayed curved C-mode image.

Figure 13A:
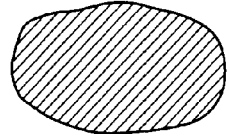
FIGS. 13A to 13D are respectively a conceptual diagram showing an example of displayed curved C-mode image.
Figure 13A:
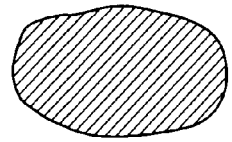
Figure 13A:
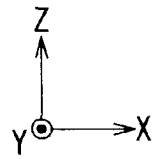
Figure 13B:
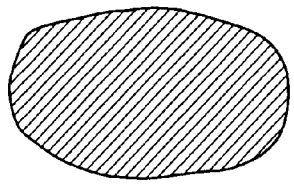
Figure 13B:
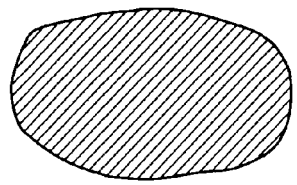
Figure 13B:
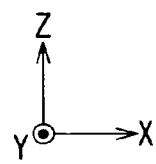
Figure 13C:
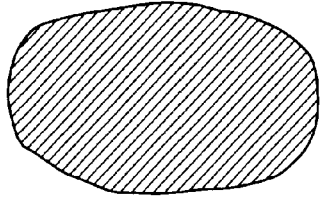
Figure 13C:
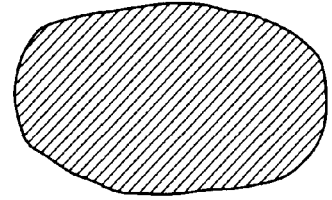
Figure 13C:
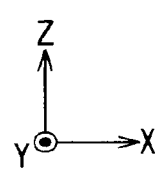
Figure 13D:
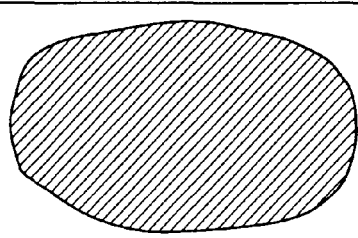
Figure 13D:
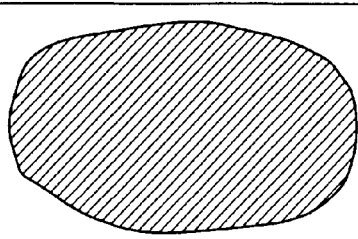
Figure 13D:
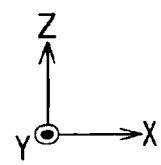

FIG. 13A shows a curved C-mode image of the curved C-mode surface C1 (shown in FIG. 6) generated by the curved C-mode surface generating unit 42. FIG. 13B shows a curved C-mode image of the curved C-mode surface C2 (shown in FIG. 6) generated by the curved C-mode surface generating unit 42. FIG. 13C shows a curved C-mode image of the curved C-mode surface C3 (shown in FIG. 6) generated by the curved C-mode surface generating unit 42. In addition, FIG. 13D shows a curved C-mode image of the curved C-mode surface C4 (shown in FIG. 6) generated by the curved C-mode surface generating unit 42. Additionally, FIGS. 13A to 13D show curved C-mode surfaces C including both of the breasts of the patient.

As shown in FIGS. 13A to 13D, since image data of curved C-mode images does not include a thorax surface, and the image of the sternum does not appear, the entire image data of the curved C-mode images can be used for diagnosis of breasts.

In addition, the curved C-mode image storage control unit 44 shown in FIG. 2 has a function to store image data of curved C-mode images generated by the curved C-mode image generating unit 43 in a storage device, such as the generic memory 32 or the HD 33.

Additionally, programs executed by the CPU 31 shown in FIG. 1 can be provided as so-called package software. Accordingly, a computer (not shown), other than the ultrasonic diagnostic apparatus 10, such as a viewer, connected to the network N may function as the corresponding units 41 to 44 shown in FIG. 2.

Figure 14:
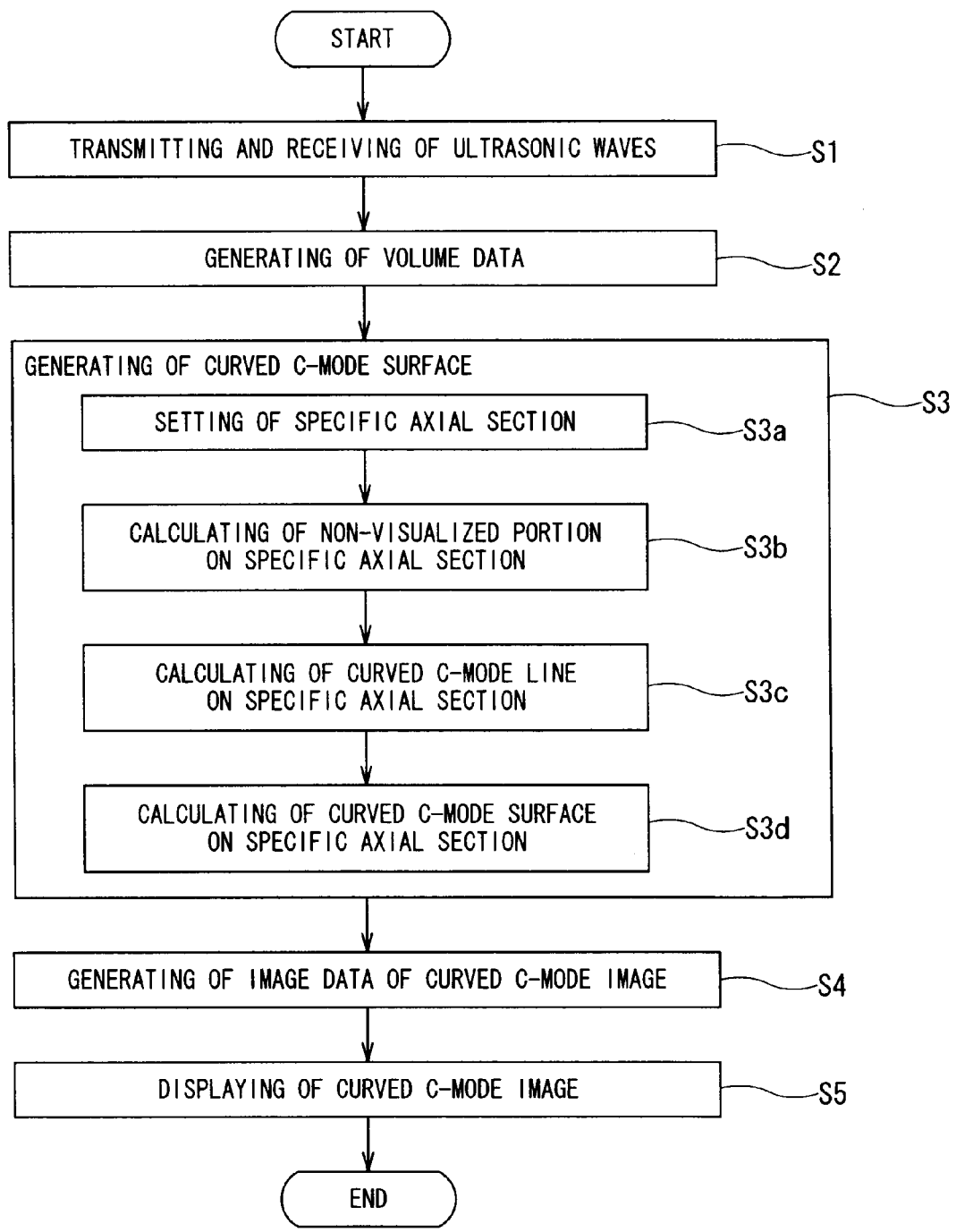
FIG. 14 is a flowchart showing an operation of the ultrasonic diagnostic apparatus according to the embodiment.

An operation of the ultrasonic diagnostic apparatus 10 according to the embodiment will be described with reference to a flowchart shown in FIG. 14.

The CPU 31 executes programs to control the transmission/reception circuit 21, the B-mode processing circuit 22, and the cine memory 23, thereby ultrasonic waves are transmitted and received by the ultrasonic probe 11 (step S1) in order to acquire volume data of a living body. Next, the RAW data of live images corresponding to a plurality of frames is stored in the cine memory 23.

Subsequently, the volume data is generated (reconstructed) by three-dimensionally rearranging ultrasonic scan line signal sequences based on the RAW data stored in the cine memory 23 (step S2).

Subsequently, the curved C-mode surface formed by the curved surface that curves without including a non-visualized portion is generated based on the volume data generated by step S2 (step S3). More specifically, step S3 includes steps S3a to S3d.

At step S3, the specific axial section, for example, the mamillary section of the patient is first set based on the volume data generated by step S2 (step S3a). The specific axial section is set automatically using image recognition by step S3a. Alternatively, an operator selects image data of a desired axial section using the input device 35 while watching images of a plurality of axial sections generated and displayed based on the volume data, whereby the specific axial section is set manually.

Subsequently, the non-visualized portion on the specific axial section, e.g., the thorax line formed on the body surface is calculated based on the image data of the specific axial section set by step S3a (step S3b).

Subsequently, the curved C-mode line on the specific axial section is calculated based on the calculated thorax line on the specific axial section determined by step S3b (step S3c).

Subsequently, the curved C-mode surface is calculated based on the curved C-mode line on the specific axial section determined by step S3c (step S3d). More specifically, the curved C-mode surface is calculated by horizontally moving the curved C-mode line on the specific axial section in the axial direction (in the Z-axis direction).

Subsequently, the image data of the curved C-mode image is generated by converting the RAW data of the curved C-mode surface generated by step S3 into the standard TV signal (step S4). The curved C-mode image is displayed on the monitor 26 through the image combining circuit 25 (step S5). FIGS. 12A to 12D and FIGS. 13A to 13D show display examples of the curved C-mode images.

Although a configuration (steps) of generating image data of a curved C-mode image based on image data of a set axial section has been described in the embodiment, the present invention is not limited to such a case. Image data of a curved C-mode image may be generated based on image data of a sagittal section and other sections.

The ultrasonic diagnostic apparatus 10 according to the embodiment can provide images suitable for diagnosis of breasts by displaying the curved C-mode surfaces C1 to C4 including the breast of the patient on the monitor 26.

What is claimed is:

1. A breast ultrasonic diagnostic apparatus for generating image data of an image of an examination-target portion based on volume data generated through an ultrasonic scan of an object and for displaying the image, the ultrasonic diagnostic apparatus comprising:
    a curved surface generating unit configured to generate, on the basis of the volume data, a curved surface formed to avoid a thorax, wherein the generated curved surface is a curved plane generated to avoid the thorax, but passes through a breast of the object, wherein the curved surface generating unit includes
        a curved line calculating unit configured to calculate a curved line on a first section that includes the breast based on a thorax line on the first section; and
        a curved surface calculating unit configured to calculate the curved surface based on the curved line determined by the curved line calculating unit; and
    a curved image generating unit configured to generate image data of a curved image based on data of the curved surface generated by the curved surface generating unit,
    wherein the curved surface calculating unit is configured to calculate the curved surface formed by moving the curved line, determined by the curved line calculating unit, in a direction orthogonal to the first section.

2. The breast ultrasonic diagnostic apparatus according to claim 1, wherein the curved surface generating unit further includes:
    a section setting unit configured to set, on the basis of the generated volume data, the first section that includes the breast; and
    a thorax line calculating unit configured to calculate the thorax line of the thorax on the first section on the basis of image data of the first section set by the section setting unit.

3. The breast ultrasonic diagnostic apparatus according to claim 2, wherein the section setting unit is configured to set the first section including a mamilla as the object, on the basis of the generated volume data.

4. The breast ultrasonic diagnostic apparatus according to claim 2, wherein the section setting unit is configured to automatically set the first section using image recognition.

5. The breast ultrasonic diagnostic apparatus according to claim 2, wherein the thorax line calculating unit is configured to calculate, as the thorax line, an arc decided by three or more points on the image data of the first section set by the section setting unit.

6. The breast ultrasonic diagnostic apparatus according to claim 2, wherein the thorax line calculating unit is configured to calculate, as the thorax line, an arc of a circle decided by two or more points on the image data of the first section set by the section setting unit and an angle between a horizontal line and a tangent passing through one of the two or more points.

7. The breast ultrasonic diagnostic apparatus according to claim 2, wherein the thorax line calculating unit is configured to calculate, as the thorax line, a line smoothly connecting a plurality of points manually set by an operator and set on a basis of a difference of luminance values on an image of a mamillary section as the first section.

8. The breast ultrasonic diagnostic apparatus according to claim 2, wherein the thorax line calculating unit is configured to calculate, as the thorax line, a line smoothly connecting a plurality of points set on a basis of a difference of luminance values on an image of a mamillary section as the first section.

9. The breast ultrasonic diagnostic apparatus according to claim 2, wherein the curved line calculating unit is configured to change a curvature of the curved line.

10. The breast ultrasonic diagnostic apparatus according to claim 2, wherein the curved line calculating unit is configured to change a thickness between a plurality of curved lines.

11. A breast ultrasonic diagnostic method for generating image data of an image of an examination-target portion based on volume data generated through an ultrasonic scan of an object and for displaying the image, the method comprising:
    a curved surface generating step of generating, on the basis of the volume data stored in a storage, a curved surface formed to avoid a thorax, wherein the generated curved surface is a curved plane generated to avoid the thorax, but passes through a breast of the object, wherein the curved surface generating step include a curved line calculating step of calculating a curved line on a first section including the breast based on a thorax line on the first section; and a curved surface calculating step of calculating the curved surface based on the curved line determined by the curved line calculating step; and a curved image generating step of generating image data of a curved image based on data of the curved surface generated by the curved surface generating step, and displaying the curved image on a display, wherein the curved surface calculating step includes calculating the curved surface formed by moving the curved line determined by the curved line calculating step, in a direction orthogonal to the first section.

12. The breast ultrasonic diagnostic method according to claim 11, wherein the curved surface generating step further includes:

a section setting step of setting, on the basis of the generated volume data, the first section including the breast; and a thorax line calculating step of calculating the thorax line of the thorax on the first section on the basis of the image data of the first section set by the section setting step.

13. The breast ultrasonic diagnostic method according to claim 12, wherein the section setting step includes setting the first section including a mamilla as the object, on the basis of the generated volume data.

14. The breast ultrasonic diagnostic method according to claim 12, wherein the section setting step includes automatically setting the first section using image recognition.

15. The breast ultrasonic diagnostic method according to claim 12, wherein the thorax line calculating step includes calculating, as the thorax line, an arc decided by three or more points on the image data of the first section set by the section setting step.

16. The breast ultrasonic diagnostic method according to claim 12, wherein the thorax line calculating step includes calculating, as the thorax line, an arc of a circle decided by two or more points on the image data of the first section set by the section setting step and an angle between a horizontal line and a tangent passing through one of the two or more points.

17. The breast ultrasonic diagnostic method according to claim 12, wherein the thorax line calculating step includes calculating, as the thorax line, a line smoothly connecting a plurality of points manually set by an operator and set on a basis of a difference of luminance values on an image of a mamillary section as the first section.

18. The breast ultrasonic diagnostic method according to claim 12, wherein the thorax line calculating step includes calculating, as the thorax line, a line smoothly connecting a plurality of points set on a basis of a difference of luminance values on an image of a mamillary section as the first section.

19. The breast ultrasonic diagnostic method according to claim 12, wherein a curvature of the curved line can be changed in the curved line calculating step.

20. The breast ultrasonic diagnostic method according to claim 12, wherein a thickness between a plurality of curved lines can be changed in the curved line calculating step.

21. The breast ultrasonic diagnostic apparatus according to claim 2, wherein the section setting unit is configured to set, on the basis of the generated volume data, the first section orthogonal to a body axis of the object.

22. The breast ultrasonic diagnostic method according to claim 12, wherein the section setting step sets, on the basis of the generated volume data, the first section orthogonal to a body axis of the object.

* * * * *